US006995302B1

(12) United States Patent
Kojima et al.

(10) Patent No.: US 6,995,302 B1
(45) Date of Patent: Feb. 7, 2006

(54) GENE REGULATING PLANT BRANCHING, VECTOR CONTAINING THE GENE, MICROORGANISM TRANSFORMED BY THE VECTOR, AND METHOD FOR REGULATING PLANT BRANCHING BY USING THE MICROORGANISM

(75) Inventors: Mineo Kojima, 3-3-12, Tokida, Ueda-shi, Nagano 386-0018 (JP); Takuji Sasaki, Tsukuba (JP); Masayuki Nozue, Nagano (JP); Hidenari Shioiri, Ueda (JP)

(73) Assignees: Kumiai Chemical Industry Co., Ltd., Tokyo (JP); Mineo Kojima, Nagano (JP)

( * ) Notice: Subject to any disclaimer, the term of this patent is extended or adjusted under 35 U.S.C. 154(b) by 490 days.

(21) Appl. No.: 10/048,990

(22) PCT Filed: Aug. 18, 2000

(86) PCT No.: PCT/JP00/05537

§ 371 (c)(1),
(2), (4) Date: May 30, 2002

(87) PCT Pub. No.: WO01/14559

PCT Pub. Date: Mar. 1, 2001

(30) Foreign Application Priority Data

Aug. 19, 1999 (JP) ................................. 11/232318

(51) Int. Cl.
*C12N 15/29* (2006.01)
*C12N 15/82* (2006.01)
*C12N 15/87* (2006.01)
*A01H 5/00* (2006.01)
*A01H 5/04* (2006.01)

(52) U.S. Cl. ...................... 800/298; 800/278; 800/290; 800/287; 800/323; 800/321; 435/468; 435/320.1

(58) Field of Classification Search ................ 526/23.1, 526/23.6; 435/468, 320.1, 471; 800/278, 800/298, 290, 287, 323, 231
See application file for complete search history.

(56) References Cited

U.S. PATENT DOCUMENTS 5,811,536 A   9/1998   Yanofsky 5,859,326 A   1/1999   An

FOREIGN PATENT DOCUMENTS

| WO | WO 96/11566 | 4/1996 |
|----|-------------|--------|
| WO | 97/27287    | 7/1997 |
| WO | WO 97/27287 | 7/1997 |
| WO | 97/46077    | 12/1997 |
| WO | 97/46078    | 12/1997 |
| WO | 97/46079    | 12/1997 |
| WO | WO 97/46077 | 12/1997 |
| WO | WO 97/46078 | 12/1997 |
| WO | WO 97/46079 | 12/1997 |
| WO | WO 98/54328 | 12/1998 |

OTHER PUBLICATIONS

Kang et al (1995, Plant Molecular Biology 29(1):1-10).*
Riechmann et al (1997, Biol. Chem. 378:1079-1101).*
Shinozuka et al (Jun. 1999, NCBI Accession No. AB003325).*
M. Kojima, et al., Plant Biotechnology, vol. 17, No. (1), pp. 35-42, XP-009007954, "Buckwheat Transformed With cDNA of a Rice MADS Box Gene is Stimulated in Branching", 2000.
T. Sasaki, Database EMBL Online !, 2 pages, XP-002234978, "DATABASE Accession No. AB003325", Jun. 30, 1999.
Y. Moon et al.: "Determination of the motif responsible for Interaction between the rice APETALA1/AGAMOUS-LIKE9 family proteins using a yeast two-hybrid system" Plant Physiology, vol. 120, pp. 1193-1204 Aug. 1999.

* cited by examiner

*Primary Examiner*—Amy J. Nelson
*Assistant Examiner*—Stuart F. Baum
(74) *Attorney, Agent, or Firm*—Oblon, Spivak, McClelland, Maier & Neustadt, P.C.

(57) ABSTRACT

Providing a technique regulating branching in ornamental plants or agricultural plants for elevating the branching and the like, to raise the value or elevate the yield.

A gene regulating plant branching, the gene containing the rice MADS box gene or a gene homologous with the gene; a vector carrying the gene; and a microorganism transformed with the vector and a method for regulating plant branching, utilizing the microorganism.

18 Claims, 12 Drawing Sheets

FIG. 5A
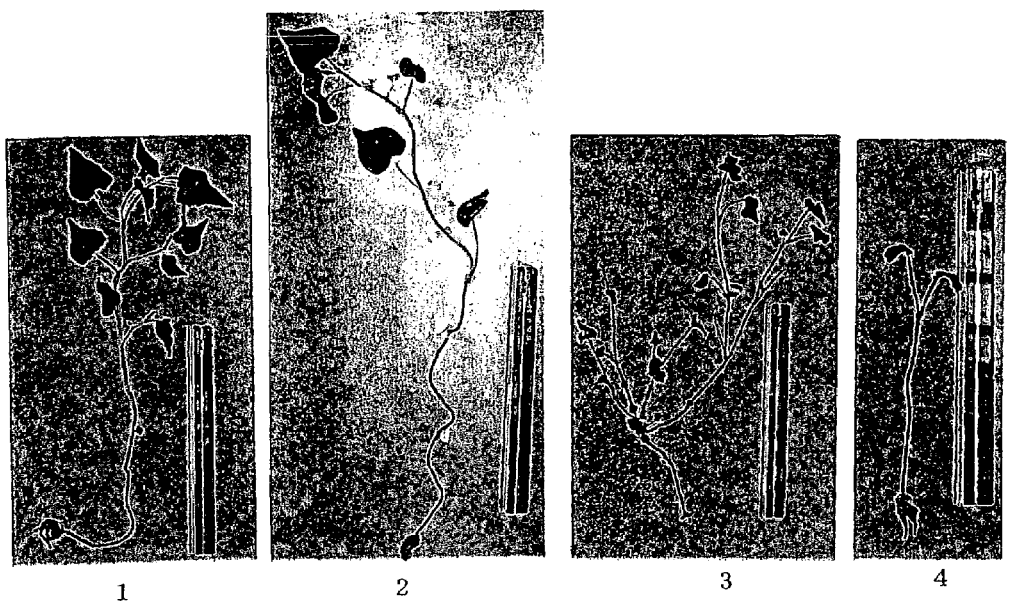
1  2  3  4
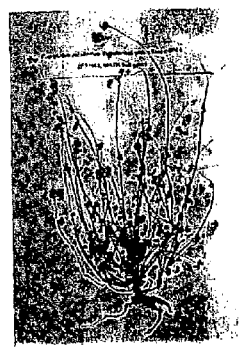
FIG. 5B

*FIG. 6A*
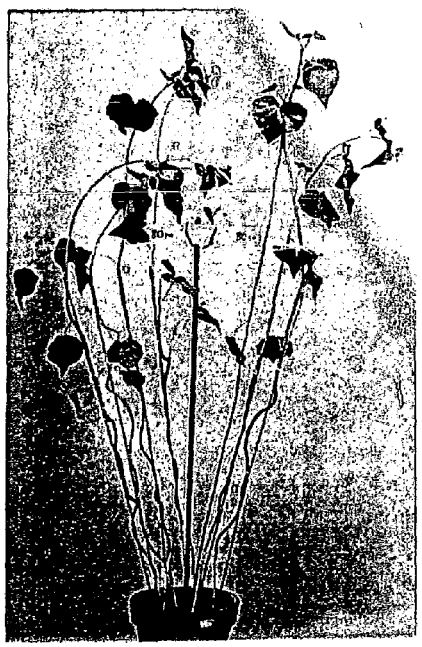
*FIG. 6B*
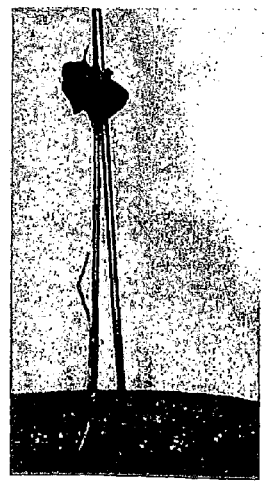

Genomic Southern Hybridization Analysis of *Fagopyrum esculentum* (T1 Plant) Transformed with a Rice MADS Box Gene in Sense Orientation Probe: $^{32}$P-labeled MADS Box gene
Lane1: Non-transformed, digested with *EcoR* I
Lane2: Transformed, digested with *EcoR* I
Lane3: Transformed, digested with *Sac* I
Lane4: Transformed, digested with *Xho* I
Lane5: Transformed, digested with *Sal* I Genomic Southern Hybridization Analysis of *Fagopyrum esculentum* (T1 Plant) Transformed with a Rice MADS Box Gene in Anti-sense Orientation

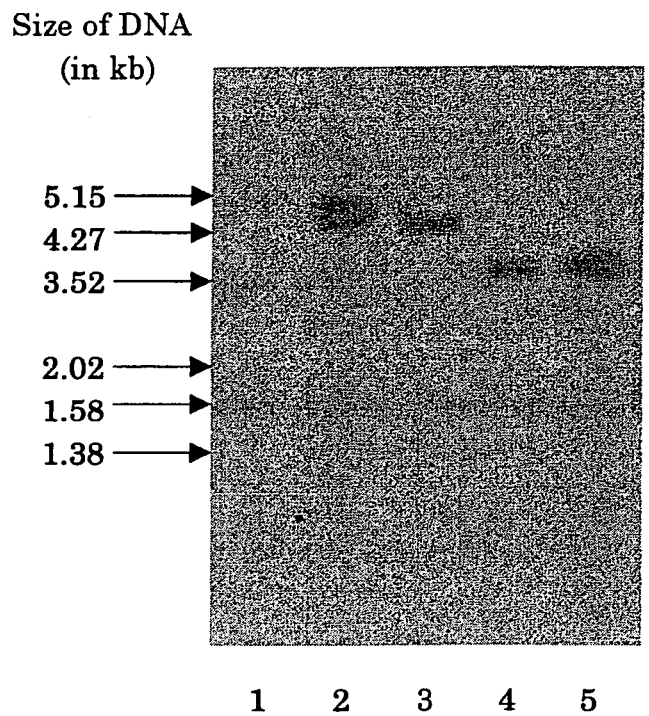

Probe: $^{32}$P-labeled MADS Box gene
Lane1: Non-transformed, digested with *EcoR* I
Lane2: Transformed, digested with *EcoR* I
Lane3: Transformed, digested with *Sac* I
Lane4: Transformed, digested with *Xho* I
Lane5: Transformed, digested with *Sal* I

*FIG. 8*

Lane 1: marker

Lane 2: pBI121-MS

Lane 3: transformed *Fagopyrum esculentum* var. Shinano No. 1 (in sense direction)

Lane 4: transformed *Fagopyrum esculentum* var. Shinano No. 1 (in antisense direction)

Lane 1: pBI121-MA

Lane 2: pBI121-MS

Lane 3: transformed *Fagopyrum esculentum* var. Shinano ichigo (in antisense direction)

Lane 4: transformed *Fagopyrum esculentum* var. Shinano ichigo (in sense direction)

FIG. 12
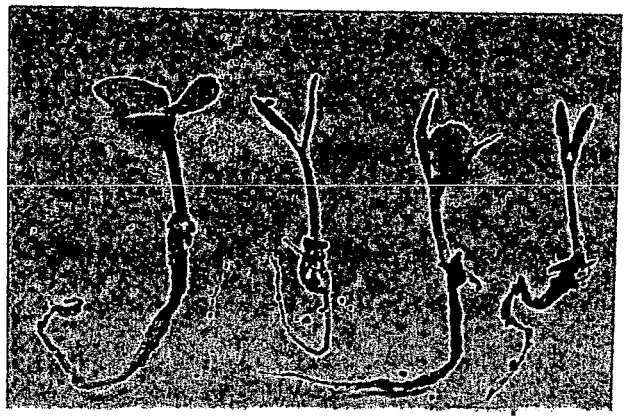
NON-TREATED KALANCHOE DAIGREMONTIANA
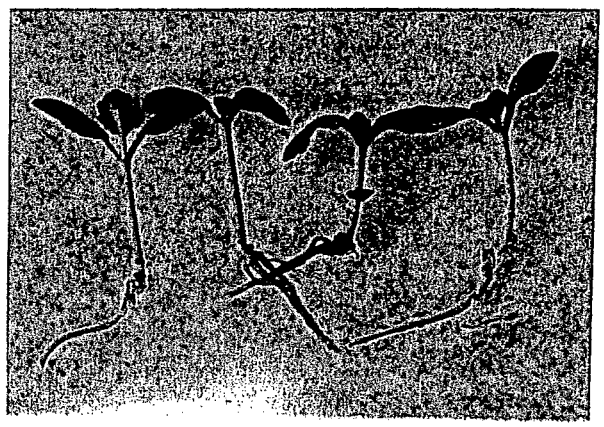
GUS GENE-INTRODUCED KALANCHOE DAIGREMONTIANA
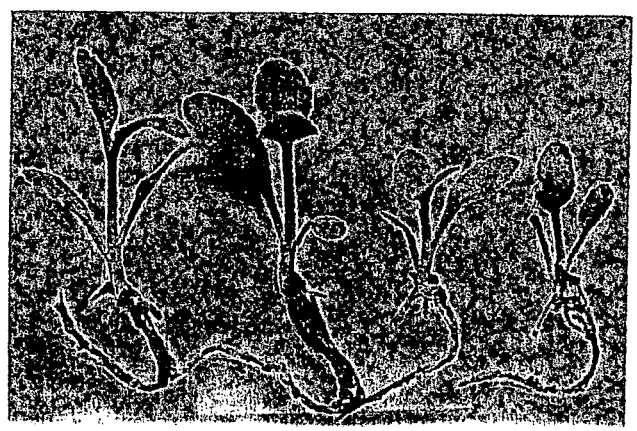
INVENTIVE GENE-INTRODUCED KALANCHOE DAIGREMONTIANA

SEQUENCE LISTING

<160> NUMBER OF SEQ ID NOS: 4

<210> SEQ ID NO 1
<211> LENGTH: 1289
<212> TYPE: DNA
<213> ORGANISM: Oryza sativa

<400> SEQUENCE: 1

```
ctcctcctcc tcttcttctt cttccactag ctagttcgtc ttcctccttc agctagcttg    60
tagcagctaa ggttaggtcg gatcgagatc gggatcggcc gccggcgagc ggcgagcggc   120
gaggatgggg cggggaagg tgcagctgaa gcggatagag aacaagatca acaggcaggt   180
gacgttctcc aagaggagga atggattgct gaagaaggcg cacgagatct ccgtcctctg   240
cgacgccgag gtcgccgcca tcgtcttctc ccccaagggc aagctctacg agtacgccac   300
tgactccagg atggacaaaa tccttgaacg ttatgagcgc tattcatatg ctgaaaaggc   360
tcttatttca gctgaatccg agagtgaggg aaattggtgc catgaataca ggaaacttaa   420
ggcaaagatt gagaccatac aaaaatgtca caaacacctc atgggagagg atctagaatc   480
cctgaatctc aaagaactcc aacagctaga gcagcagctg gagagttcat tgaagcacat   540
aatatcaaga aagagccacc ttatgcttga gtccatttcc gagctgcaga aaaggagag   600 gtcactgcag gaggagaaca aggctctgca gaaggaactg gtggagaggc agaagaatgt   660 gagggggccca cagcaagtag ggcagtggga ccaaacccag gtccaggccc aggcccaagc   720 ccaacccaa gcccagacaa gctcctcctc ctcctccatg ctgagggatc agcaggcact   780
tcttccacca caaatatct gctaccccgcc ggtgatgatg ggcgagagaa atgatgcggc   840
ggcggcggcg gcggtggcgg cgcagggcca ggtgcaactc cgcatcggag gtcttccgcc   900 atgatgctg agccacctca atgcttaaga tgatcatcgt cgtcgtcgtc ggccaaacag   960
ctgccgtatg caccgtgaat catgggagca accttgaatg aattgaagtc attggtatcg  1020
atcctagcga taatatatat gattctccta aaatgaaatt gatctcaaaa aaacaaacct  1080
agcgattaag ctattcttat atatgtgttt gcctgctgcc ccctacccta caggctacat  1140
atgatttgca agaaattaat tatgagcaag gatcaggatg tgtctttgtg taatcatcag  1200
cacgtaccta gtgcttccta ctgatatata tgcatgcaat tgtgtgcata taaatatatt  1260
tgcatgccat gctcccgtga tggttaatt                                    1289
```

<210> SEQ ID NO 2
<211> LENGTH: 267
<212> TYPE: PRT
<213> ORGANISM: Oryza sativa
<220> FEATURE:
<221> NAME/KEY: DOMAIN
<222> LOCATION: (1)..(57)
<223> OTHER INFORMATION: MADS domain
<220> FEATURE:
<221> NAME/KEY: DOMAIN
<222> LOCATION: (92)..(158)
<223> OTHER INFORMATION: K domain -continued

```
<400> SEQUENCE: 2

Met Gly Arg Gly Lys Val Gln Leu Lys Arg Ile Glu Asn Lys Ile Asn
 1               5                  10                  15

Arg Gln Val Thr Phe Ser Lys Arg Arg Asn Gly Leu Leu Lys Lys Ala
                20                  25                  30

His Glu Ile Ser Val Leu Cys Asp Ala Glu Val Ala Ala Ile Val Phe
            35                  40                  45

Ser Pro Lys Gly Lys Leu Tyr Glu Tyr Ala Thr Asp Ser Arg Met Asp
 50                  55                  60

Lys Ile Leu Glu Arg Tyr Glu Arg Tyr Ser Tyr Ala Glu Lys Ala Leu
 65                  70                  75                  80

Ile Ser Ala Glu Ser Glu Ser Glu Gly Asn Trp Cys His Glu Tyr Arg
                85                  90                  95

Lys Leu Lys Ala Lys Ile Glu Thr Ile Gln Lys Cys His Lys His Leu
            100                 105                 110

Met Gly Glu Asp Leu Glu Ser Leu Asn Leu Lys Glu Leu Gln Gln Leu
        115                 120                 125

Glu Gln Gln Leu Glu Ser Ser Leu Lys His Ile Ile Ser Arg Lys Ser
130                 135                 140

His Leu Met Leu Glu Ser Ile Ser Glu Leu Gln Lys Lys Glu Arg Ser
145                 150                 155                 160

Leu Gln Glu Glu Asn Lys Ala Leu Gln Lys Glu Leu Val Glu Arg Gln
                165                 170                 175

Lys Asn Val Arg Gly Gln Gln Val Gly Gln Trp Asp Gln Thr Gln
            180                 185                 190

Val Gln Ala Gln Ala Gln Ala Gln Pro Gln Ala Gln Thr Ser Ser Ser
        195                 200                 205

Ser Ser Ser Met Leu Arg Asp Gln Gln Ala Leu Leu Pro Pro Gln Asn
210                 215                 220

Ile Cys Tyr Pro Pro Val Met Met Gly Glu Arg Asn Asp Ala Ala Ala
225                 230                 235                 240

Ala Ala Ala Val Ala Ala Gln Gly Gln Val Gln Leu Arg Ile Gly Gly
                245                 250                 255

Leu Pro Pro Trp Met Leu Ser His Leu Asn Ala
            260                 265

<210> SEQ ID NO 3
<211> LENGTH: 20
<212> TYPE: DNA
<213> ORGANISM: Artificial Sequence
<220> FEATURE:
<223> OTHER INFORMATION: Synthetic DNA

<400> SEQUENCE: 3
acaatcccac tatccttcgc                                                 20

<210> SEQ ID NO 4
<211> LENGTH: 20
<212> TYPE: DNA
<213> ORGANISM: Artificial Sequence
<220> FEATURE:
<223> OTHER INFORMATION: Synthetic DNA

<400> SEQUENCE: 4
gtcacgacgt tgtaaaacga                                                 20
```

GENE REGULATING PLANT BRANCHING, VECTOR CONTAINING THE GENE, MICROORGANISM TRANSFORMED BY THE VECTOR, AND METHOD FOR REGULATING PLANT BRANCHING BY USING THE MICROORGANISM

TECHNICAL FIELD

The present invention relates to a gene regulating plant branching, a vector containing the gene, a microorganism transformed by the vector, and a method for regulating plant branching by using the microorganism.

BACKGROUND OF THE INVENTION

The promotion of branching in ornamental plants or agricultural plants is preferable because the value of ornamental plants and the yield of agricultural plants can be increased. Therefore, a technique for regulating branching in various plants has been desired.

Maize tbl gene has been known as a gene regulating branching (J. Doebley et al., "Nature" 386, 485–488 (1997)). The gene is a gene functioning to suppress branching. Alternatively, only the zinc finger gene has been reported as a gene promoting branching (H. Takatsuji, "Plant Mol. Biol. (review)" 39, 1073–1078, (1999) and Hiroshi Takatsuji, "Kagaku to Seibutsu", Vol. 37, pp. 287–289 (1999)).

As described above, promotion of branching serves for elevating the values of ornamental plants or agricultural plants so that these techniques are significant techniques in the field of agriculture and floriculture. However, it cannot be said that these techniques are applicable to all plants, bringing about a great outcome. Hence, another new technique for promoting branching is strongly desired.

Further, the suppression of plant growth to thereby produce a dwarf plant of a short length has been performed frequently. Hence, it has been desired to provide a technique for performing the suppression in a simple manner by using gene manipulation.

Currently, only a number of genes including a gene isolated from the chromosomal DNA of *Arabidopsis thaliana* have been known as such gene controlling plant dwarfism (Japanese Patent Laid-open No. 56382/1997).

The invention has been achieved in the technical state of art as described above. It is a purpose of the invention to provide a technique regulating the branching of plants such as ornamental plants and agricultural plants.

DISCLOSURE OF THE INVENTION

The inventors have screened a lot of genes to find out a gene controlling plant branching. The inventors have finally found that the rice MADS box gene has a function to regulate plant branching.

Also, the inventors have found that in plants transformed by a vector with the gene via an appropriate host microorganism, branching or dwarfism is promoted depending on the gene direction. Thus, the invention has been achieved.

Specifically, the invention provides a gene regulating plant branching, where the gene is characterized by containing the rice MADS box gene or a gene homologous with the gene.

Additionally, the invention provides a vector with the gene integrated therein and a microorganism transformed with the vector.

Still additionally, the invention provides a method for regulating plant branching, where the method is characterized by integrating the rice MADS box gene or a gene homologous with the gene into a vector and transferring the vector via a host microorganism into a plant.

BRIEF DESCRIPTION OF THE DRAWINGS

FIGS. 5A and 5B show photographs depicting the appearance of *Fagopyrum esculentum* var. *Shinano ichigo*, where the inventive gene is introduced toward the sense and antisense directions.

FIGS. 6A and 6B show photographs depicting the comparison in appearance among *Fagopyrum esculentum* var. *Shinano ichigo* individuals where the inventive gene is introduced toward the sense and antisense directions and *Fagopyrum esculentum* var. *Shinano ichigo* with no treatment.

FIG. 8 is an image depicting the results of the genomic Southern hybridization of *Fagopyrum esculentum* var. *Shinano* No. 1 (T1) where the inventive gene is introduced toward the antisense direction.

FIG. 12 shows photographs depicting the comparison in appearance among *Kalanchoe daigremontiana* where the inventive gene is introduced toward the sense direction, *Kalanchoe daigremontiana* where the GUS gene is introduced and *Kalanchoe daigremontiana* with no treatment.

BEST MODE FOR CARRYING OUT THE INVENTION

Figure 1:
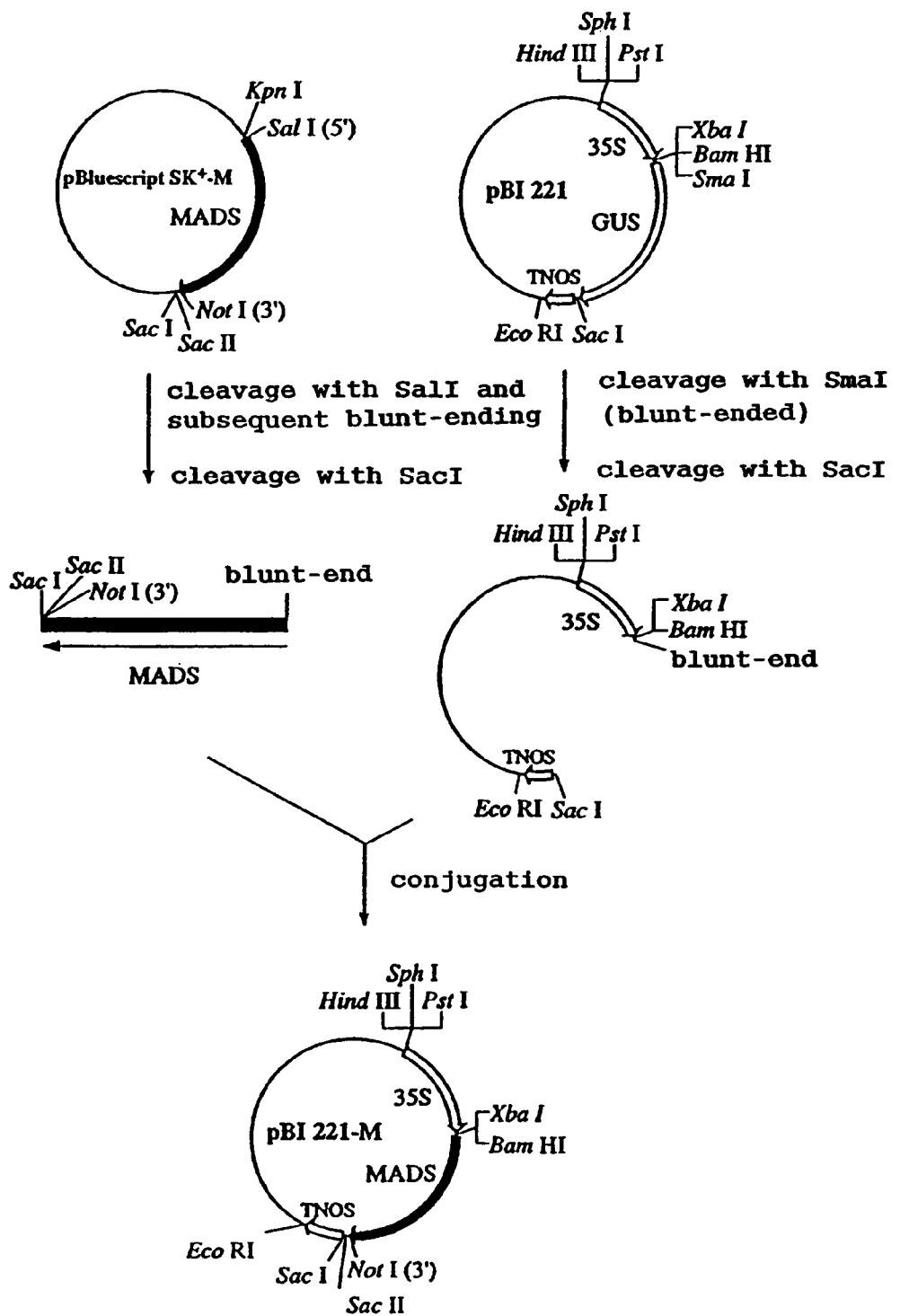
FIG. 1 depicts the former half of the method for construction of the sense vector in accordance with the invention.

The gene to be used as a gene regulating plant branching in accordance with the invention includes the rice MADS box gene or a gene homologous with the gene. The rice MADS box gene has the following nucleotide sequence (SEQ ID NO: 1):

ctcctcctcc tcttcttctt cttccactag ctagttcgtc ttcctccttc agctagcttg tagcagctaa ggttaggtcg gatcgagatc gggatcggcc gccggcgagc ggcgagcggc gaggatgggg cgggggaagg tgcagctgaa gcggatagag aacaagatca acaggcaggt gacgttctcc aagaggagga atggattgct gaagaaggcg cacgagatct ccgtcctctg cgacgccgag gtcgccgcca tcgtcttctc ccccaagggc aagctctacg agtacgccac tgactccagg atggacaaaa tccttgaacg ttatgagcgc tattcatatg ctgaaaaggc tcttatttca gctgaatccg agagtgaggg aaattggtgc catgaataca ggaaacttaa ggcaaagatt gagaccatac aaaaatgtca caaacacctc atgggagagg atctagaatc cctgaatctc aaagaactcc aacagctaga gcagcagctg gagagttcat tgaagcacat aatatcaaga aagagccacc ttatgcttga gtccatttcc gagctgcaga aaaggagag gtcactgcag gaggagaaca aggctctgca gaaggaactg gtggagaggc agaagaatgt gaggggccag cagcaagtag ggcagtggga ccaaacccag gtccaggccc aggcccaagc ccaaccccaa gcccagacaa gctcctcctc ctcctccatg ctgagggatc agcaggcact tcttccacca caaatatct gctacccgcc ggtgatgatg ggcgagagaa atgatgcggc ggcggcggcg gcggtggcgg cgcagggcca ggtgcaactc cgcatcggag gtcttccgcc atggatgctg agccacctca atgcttaaga tgatcatcgt cgtcgtcgtc ggccaaacag ctgccgtatg caccgtgaat catgggagca accttgaatg aattgaagtc attggtatcg atcctagcga taatatatat gattctccta aaatgaaatt gatctcaaaa aaacaaacct agcgattaag ctattcttat atatgtgttt gcctgctgcc ccctacccta caggctacat atgatttgca agaaattaat tatgagcaag gatcaggatg tgtctttgtg taatcatcag cacgtaccta gtgcttccta ctgatatata tgcatgcaat tgtgtgcata taaatatatt tgcatgccat gctcccgtga tggttaatt Further, the term "gene homologous with the gene" includes a range of genes, which are not identical to the latter gene per se due to the results of the presence of substitution, deletion, insertion or the like in a part of the nucleotide sequences but can be assumed identical in terms of the functions exerted by the genes.

Among the amino acids encoded by the gene, it is elucidated that a peptide part represented by the following sequence (SEQ ID NO: 2) regulates branching as a transcription factor:

```
                                                          20
MetGlyArgGlyLysValGlnLeuLysArgIleGluAsnLysIleAsnArgGlnValThr

40
PheSerLysArgArgAsnGlyLeuLeuLysLysAlaHisGluIleSerValLeuCysAsp

60
AlaGluValAlaAlaIleValPheSerProLysGlyLysLeuTyrGluTyrAlaThrAsp

80
SerArgMetAspLysIleLeuGluArgTyrGluArgTyrSerTyrAlaGluLysAlaLeu

100
IleSerAlaGluSerGluSerGluGlyAsnTrpCysHisGluTyrArgLysLeuLysAla

120
LysIleGluThrIleGlnLysCysHisLysHisLeuMetGlyGluAspLeuGluSerLeu
```

-continued

```
                                140
AsnLeuLysGluLeuGlnGlnLeuGluGlnGlnLeuGluSerSerLeuLysHisIleIle

160
SerArgLysSerHisLeuMetLeuGluSerIleSerGluLeuGlnLysLysGluArgSer

180
LeuGlnGluGluAsnLysAlaLeuGlnLysGluLeuValGluArgGlnLysAsnValArg

200
GlyGlnGlnGlnValGlyGlnTrpAspGlnThrGlnValGlnAlaGlnAlaGlnAlaGln

220
ProGlnAlaGlnThrSerSerSerSerSerSerMetLeuArgAspGlnGlnAlaLeuLeu

240
ProProGlnAsnIleCysTyrProProValMetMetGlyGluArgAsnAspAlaAlaAla

260
AlaAlaAlaValAlaAlaGlnGlyGlnValGlnLeuArgIleGlyGlyLeuProProTrp

267
MetLeuSerHisLeuAsnAla
```

Accordingly, the term "MADS" of the MADS gene is the acronym of "M" of yeast MCM1, "A" of plant AGAMOUS, "D" of plant DEFICIENS, and "S" of human serum response factor SRF. Thus MADS box genes are found out to have a common nucleotide sequence, disregard the type of species. These genes are transcription factors (gene regulating DNA so that DNA might be transcribed into mRNA), like a gene involved in biological morphology, namely homeotic gene.

Further, most of the MADS genes of plants excluding rice are involved in flower morphology, but none of them is known to be involved in the regulation of plant branching.

In accordance with the invention, the gene regulating plant branching (referred to as "inventive gene") is integrated in a vector, which is then introduced via an appropriate host microorganism into a plant, to regulate plant branching. More specifically, a plant cell is transformed by conjugating a promoter capable of functioning in a plant cell, the inventive gene and a terminator capable of functioning in a plant cell in a manner such that the resulting conjugate can function to construct an expression plasmid and then introducing the expression plasmid into the plant cell.

As the promoter for use for that purpose, for example, a CaMV35S promoter and a promoter for nopaline synthase can be utilized, with no specific limitation. Additionally, an enhancer can be used for high expression of the gene product. As such enhancer, for example, the enhancer contained in the sequence in an upstream region of the nucleotide sequence of the CaMV35S promoter can be utilized. A plurality of such enhancers can be used. Alternatively, the terminator includes but is not limited to a CaMV35S terminator and a terminator for nopaline synthase.

In accordance with the invention, a selection marker gene can be utilized for ready screening of the resulting transformant microorganism and transformant plant.

Selection markers can be used, including for example neomycin phosphotransferase 2 (MPT2) gene and hygromycin phosphotransferase (HPT) gene.

As the vector for use in the integration of the inventive gene in accordance with the method of the invention, vectors of pBI series and pUC series can preferably be used. The vectors of the pBI series include for example pBI121, pBI101, pBI101.2 and pBI101.3, while the vectors of the pUC series include for example pUC18, pUC19 and pUC9.

Further, vectors such as pTOK162 developed for the transformation of monocot plants can also be utilized.

As the method for transforming plants with the vector with the inventive gene integrated therein, the *Agrobacterium* method, the polyethylene glycol method, the electroporation method, and the particle gun method and the like can be used.

Among the transformation methods, the *Agrobacterium* method is a method for introducing a gene in a plant cell by culturing *Agrobacterium* carrying a vector harboring the recombinant gene in the concurrent presence of a plant culture cell. As a simpler method, a method for spraying or coating or injecting a solution containing the *Agrobacterium* in the proximity of plant growth point can also be utilized. Then, preferably, a scratch is made on the plant body.

The branching regulation by the method of the invention is applicable to any plant with cells, tissues or organs into which the gene can be introduced and for which the re-differentiation methods have been established, or any plant where the gene can be introduced directly in the plant body.

Specifically, transformed plants of ornamental plants such as chrysanthemum, lily, carnation, tulip, rose and orchidales, and agricultural plants such as soybean, cotton, rice, maize, wheat and barley can be recovered by treating the calli or growth points thereof with a suspension of *Agrobacterium* carrying a vector with the inventive gene integrated therein or by directly injecting a vector with the inventive gene integrated therein into the cells or tissues thereof and screening and growing a transformant.

The outcome of the invention, as described in the following Examples, varies diversely, depending on whether the inventive gene is integrated in plants toward the sense direction or whether the inventive gene is integrated in plants toward the antisense direction. In other words, plant branching is promoted when the gene is integrated toward the sense direction, while plant growth is suppressed into dwarfism when the gene is integrated toward the antisense direction.

INDUSTRIAL APPLICABILITY

The gene regulating plant branching of the invention can promote plant branching or dwarfism, when the gene is introduced into plants. Additionally, the resulting property can be inherited to the progenies. Thus, the invention is a technique for creating a plant with such new phenotype; particularly, the invention is effective for the elevation of branching in plants such as ornamental plants and agricultural plants to raise the value of the ornamental plants or the yield of the agricultural plants.

EXAMPLES

The invention will now be described below in more detail in Examples. But the invention is never limited to these Examples.

Example 1

Figure 2:
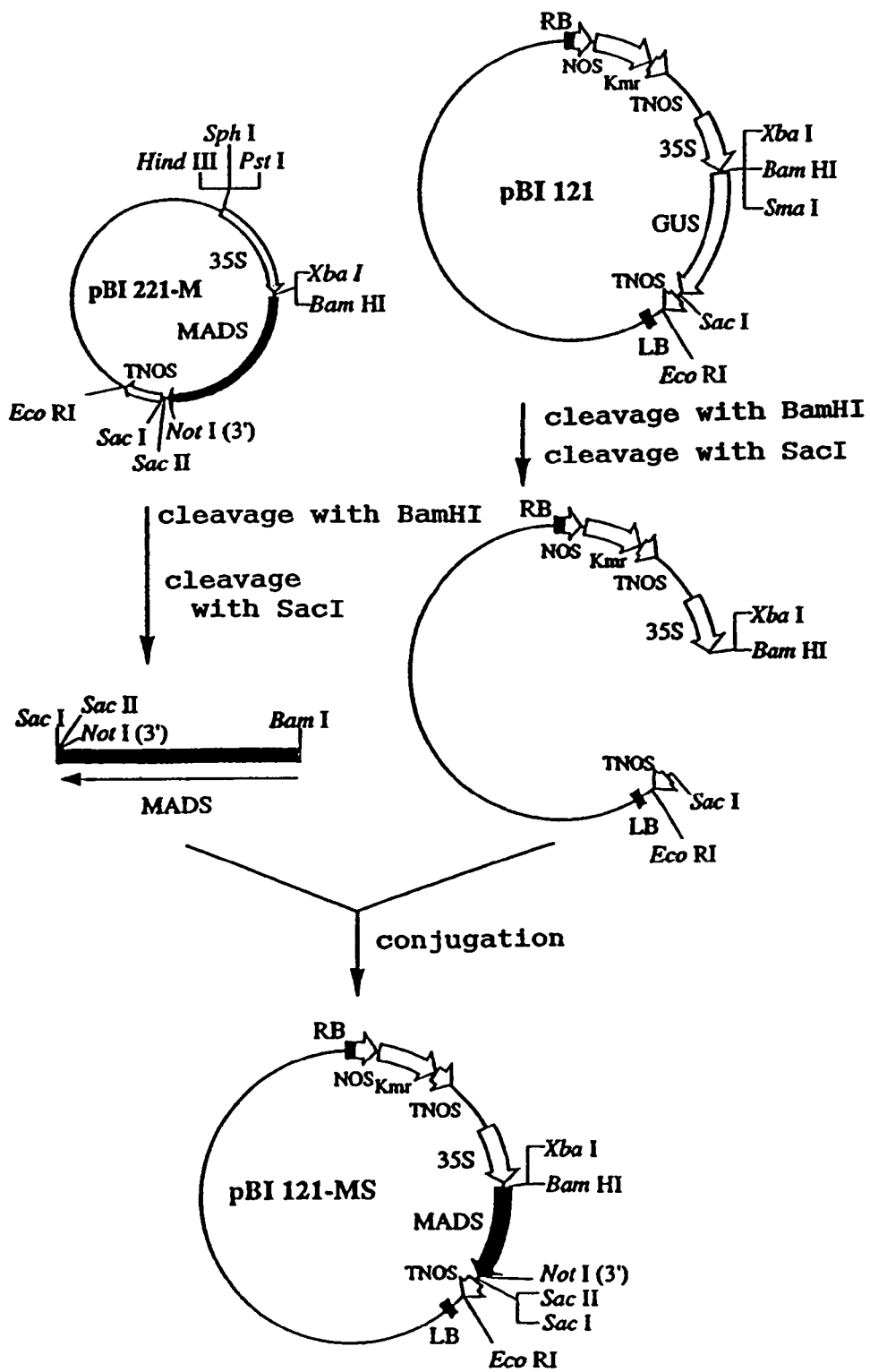
FIG. 2 depicts the latter half of the method for construction of the sense vector in accordance with the invention.

(1) Construction of a Vector with the Rice MADS Box Gene Integrated toward the Sense Direction Therein (FIGS. 1 and 2)

The vector with the rice MADS box gene integrated toward the sense direction therein was constructed by replacing the β-glucuronidase (GUS) gene in a binary vector (pBI121) purchased from Toyobo Co., Ltd. with the sense-directed cDNA (1.3 kb) of the rice MADS box gene (DDBJ accession No. AB003325) according to the following method.

The pBluescriptSK⁺M plasmid (available from the DNA bank at the National Institute of Agrobiological Sciences, the Ministry of Agriculture, Forestry and Fishery) where the MADS box gene was inserted at the restriction SalI cleavage site and the restriction NotI cleavage site from the 5'→3' direction was digested with SalI and blunt-ended, which was further digested with SacI. The resulting product was subjected to electrophoresis, to recover a 1.3-kb DNA fragment.

On the other hand, the pUC18 plasmid (manufactured by Nippon Gene/corresponding to pBI221 manufactured by Toyobo, Co., Ltd.), where a pBI121-derived 3.1-kb DNA fragment (containing the CaMV35S promoter and the GUS gene and the Nos terminator) was inserted at the restriction HindIII and EcoRI cleavage sites, was digested with SmaI and SacI. The resulting product was subjected to agarose electrophoresis, to recover a 4.0-kb DNA fragment.

pBI221-M plasmid was prepared by ligating the 1.3-kb fragment and the resulting 4.0-kb fragment together, which was then introduced in *Escherichia coli* (JM109). From the positive colonies of *Escherichia coli*, the pBI221-M plasmid was isolated and digested with BamHI and SacI, to recover the 1.3-kb cDNA. The cDNA with BamHI and SacI cleavage sites, as recovered in such manner, was conjugated with a pBI121 plasmid preliminarily digested with BamHI and SacI to eliminate the GUS gene, to recover a pBI121-MS vector where the rice MADS box gene was integrated toward the sense direction (referred to as "sense vector" hereinbelow).

Figure 3:
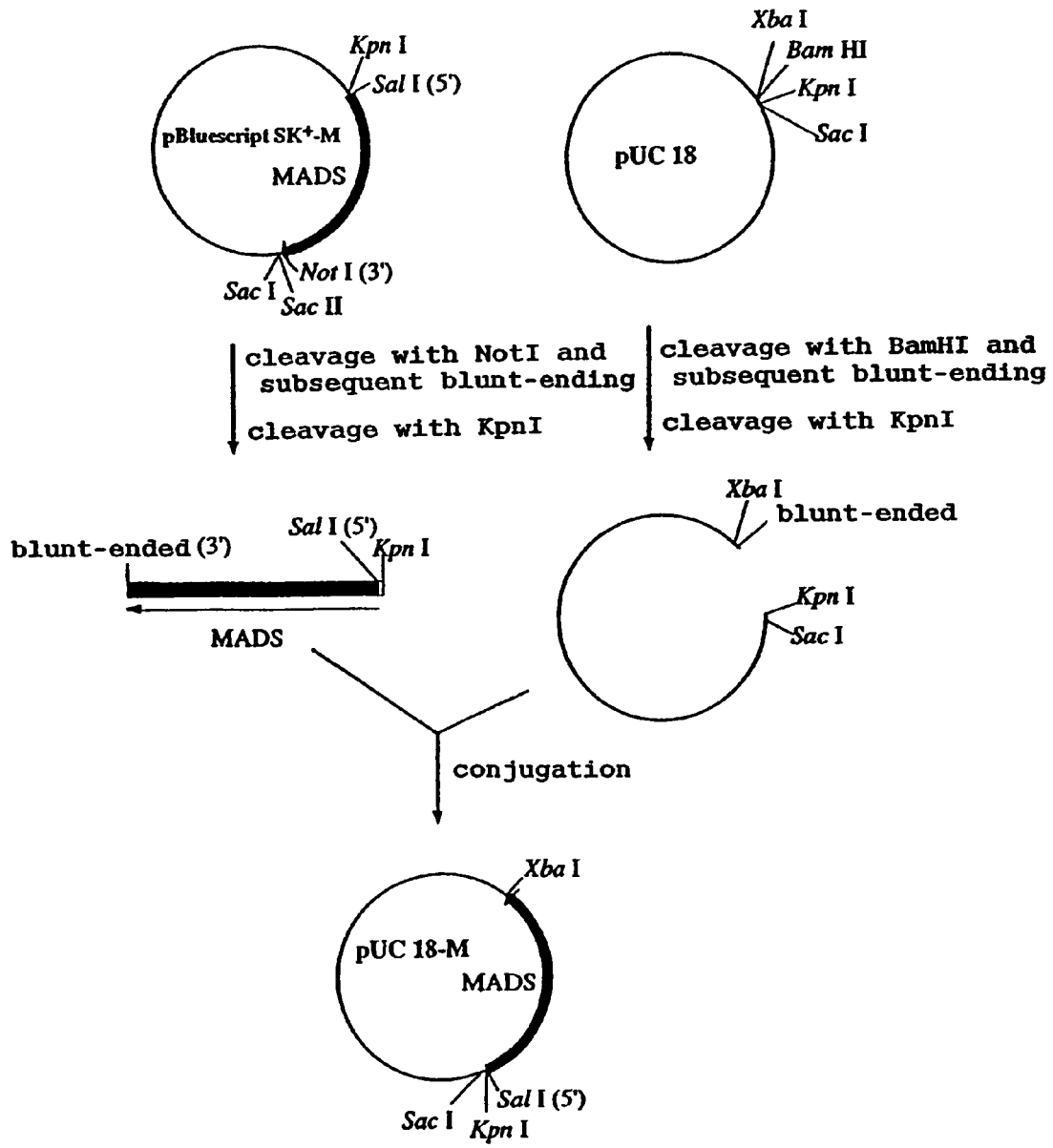
FIG. 3 depicts the former half of the method for construction of the antisense vector in accordance with the invention.
Figure 4:
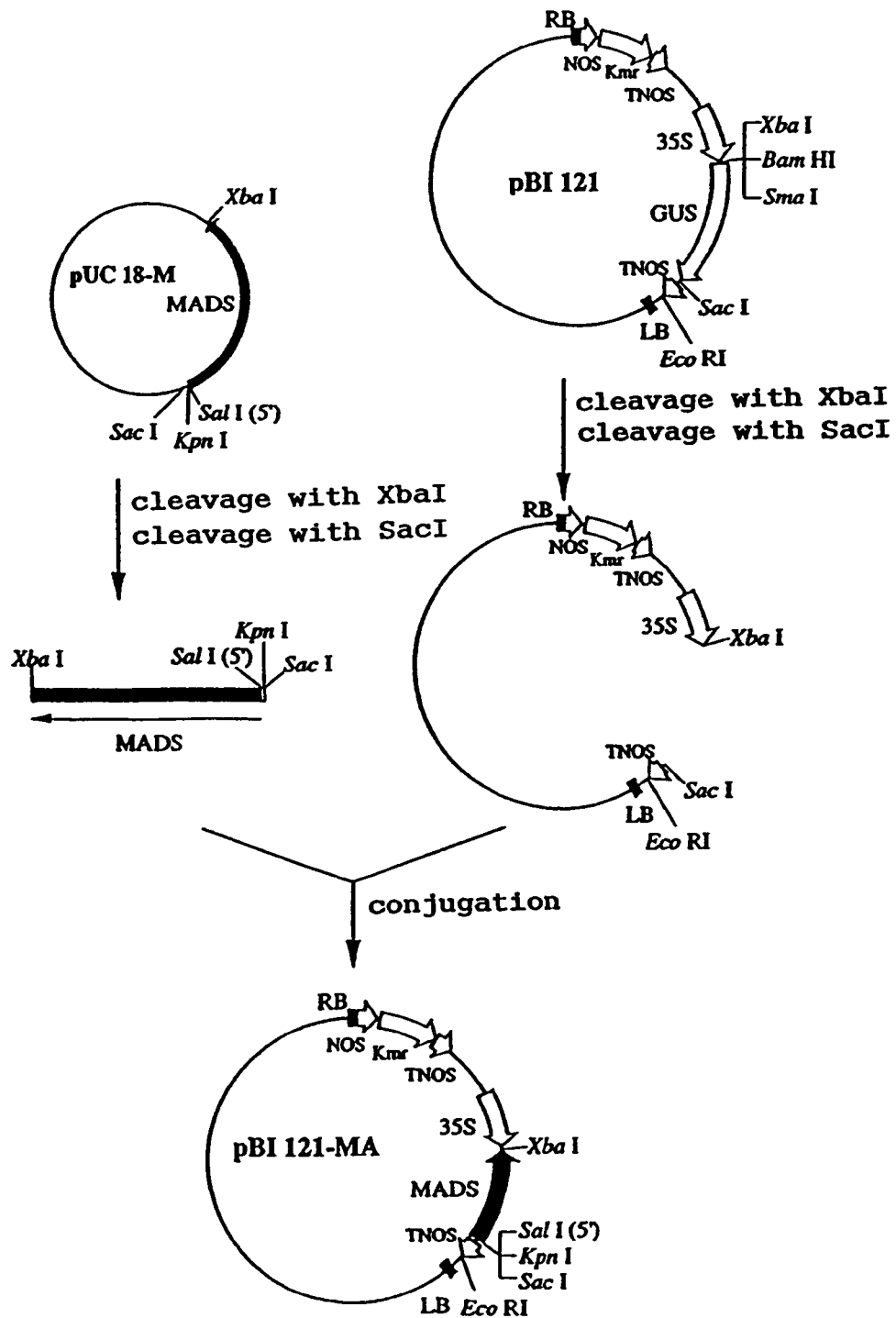
FIG. 4 depicts the latter half of the method for construction of the antisense vector in accordance with the invention.

(2) Construction of a Vector with the Rice MADS Box Gene Integrated toward the Antisense Direction Therein (FIGS. 3 and 4).

A pBI121-MA vector where the GUS gene was replaced with the cDNA in the antisense direction was prepared by the following method. First, pBluescriptSK⁺-M plasmid where the cDNA was inserted at the restriction SalI and NotI cleavage sites in the 5'→3' direction was digested with NotI and blunt-ended, followed by digestion with KpnI. The resulting product was subjected to electrophoresis, to recover a 1.3-kb DNA fragment.

On the other hand, the pUC18 plasmid was digested with BamHI and was then blunt-ended, followed by further digestion with KpnI. The product was subjected to electrophoresis, to recover a 2.6-kb DNA fragment. The fragment was conjugated with the 1.3-kb fragment, to prepare a pUC18-M plasmid, which was then introduced in *Escherichia coli* (HB101). From the positive colonies of *Escherichia coli*, the pUC18-M plasmid was isolated and digested with SacI and XbaI, to recover a 1.3-kb cDNA with SacI and XbaI cleavage sites. The cDNA was conjugated with a pBI121 vector preliminarily digested with SacI and XbaI, to recover a pBI121-MA vector where the rice MADS box gene was integrated toward the antisense direction (referred to as "antisense vector" hereinbelow).

(3) Vector Introduction into Host Microorganism

As the host microorganism, *Agrobacterium tumefaciens* (*A. tumefaciens*) LBA 4404 available from Toyobo Co., Ltd. was used. The introduction of the vector recovered above in (1) or (2) into the microorganism was performed by a previously reported method (M. Holster et al., "Mol. Gen. Gene", 163, 181–187 (1978)). After introduction, the microorganism was cultured in an LB culture medium supplemented with 50 μg/ml kanamycin, and 10 μg/ml rifampicin and 50 μg/ml streptomycin at 28° C. for 18 hours. After termination of the culture, the cells were harvested by centrifugation, and were rinsed in water and suspended in water ($1.0 \times 10^8$ cells/ml), for use in the inoculation into plants.

(4) Inoculation into Plants

The seed of *Fagopyrum esculentum* var. Shinano No. 1 was sterilized with sodium hypochlorite and was then planted in soil in a planting pot. The pot was placed under conditions of a temperature of 25° C. for 8 hours in brightness and 16 hours in darkness. Four to 5 days after seeding, two leaves of the plant were opened. Just when the plant reached a height of 7 to 8 cm, a small hole was punctured into the shoot meristem of the stem top with a needle, where the aqueous suspension (about $1.0 \times 10^8$ cells/ml) of *A. tumefaciens* carrying the vector was inoculated.

Inoculation was conducted for 50 seedling individuals of *Fagopyrum esculentum* var. Shinano No. 1, which were placed under conditions of a temperature of 22° C. for 3 days in absolute darkness. Subsequently, the individual plants were grown at 30° C. under an illumination of about 4,000 lux in a growth chamber for 8 hours. In *Fagopyrum esculentum* var. Shinano No. 1, two types of flowers with different style lengths, namely about 1.8 mm and about 0.6 mm, bloom (heterostylism; phenomenon with different styles). Pollination between the different types of flowers can lead to fertilization. So as to recover a seed (T1 plant), thus, pollination was conducted between the flower of the transformant plant (T0) and a different type of the flower of the plant with no transformation.

Among the 50 plants inoculated with *A. tumefaciens* carrying the sense vector, branching was promoted in 33 individuals of the plants, so that many branches were formed. However, the expression levels of the phenotypes of the transformants varied among the plants. No change was observed in the differentiation and structure of the flower.

Among the 50 plants inoculated with *A. tumefaciens* carrying the antisense vector, branching and growth were suppressed in 30 individuals of the plants. The expression levels of the phenotypes varied among the plants, as in the plants described above. No apparent change was observed in terms of the flower development and structure of the flowers of these plants.

FIG. 5 (photographs) depicts the appearance of *Fagopyrum esculentum* var. Shinano No. 1 with the inventive gene introduced toward the sense- and antisense directions therein. In FIG. 5(A), the sign "1" expresses *Fagopyrum esculentum* var. *Shinano* No. 1 with no treatment; the sign "2", *Fagopyrum esculentum* var. *Shinano* No. 1 treated with *A. tumefaciens* carrying the pBI121 vector (GUS gene); the sign "3", *Fagopyrum esculentum* var. *Shinano* No. 1 treated with *A. tumefaciens* carrying the sense vector; and the sign "4", *Fagopyrum esculentum* var. *Shinano* No. 1 treated with *A. tumefaciens* carrying the antisense vector. These photographs were taken one month after the treatments. Further, the bar in the photographs shows a scale of a 30-cm length.

The results show that branching was promoted in *Fagopyrum esculentum* var. *Shinano* No. 1 introduced with the inventive gene toward the sense direction (3 in FIG. 5(A)) while branching was suppressed in *Fagopyrum esculentum* var. *Shinano* No. 1 introduced with the inventive gene toward the antisense direction (4 in FIG. 5(A)).

Further, FIG. 5(B) depicts *Fagopyrum esculentum* var. *Shinano* No. 1 introduced with the inventive gene toward the sense direction at the highest transformation expression phenotype (branching level) among such *Fagopyrum esculentum* var. *Shinano* No. 1 individuals introduced with the inventive gene toward the sense direction. The photograph was taken after the plant stopped its growth and withered, 6 months after the treatment.

(5) At the test described above, *A. tumefaciens* was inoculated into the shoot meristem at the stem tops of the seedlings for transformation, with no subsequent elimination procedure for removing the *Agrobacterium* from the seedlings. Therefore, the T0 plants and the T1 plants were examined by the following method, as to whether or not the inoculated *Agrobacterium* remained, namely whether or not the morphological changes of the transformed plants were caused by the effect of *A. tumefaciens*.

The entirety of the plants (T0 plants) after inoculation was ground with sterile water in a mortar. The ground plant solution was spread on an LB culture plate containing an antibiotic capable of growing the *A. tumefaciens* used for transformation, for incubation at 28° C. The number of colonies emerging on the plate was decreased, as the time period after inoculation passed. On day 14 after inoculation, only several colonies emerged. It is suggested that a great number of the *Agrobacteria* were probably eliminated via the resistance reaction of the plant *Fagopyrum esculentum* var. *Shinano* No. 1.

In case of the T1 plants, the seeds were sterilized with sodium hypochlorite solution, for subsequent aseptic sprouting and growth. The seedlings consequently recovered were ground with sterile water and were then cultured on an LB culture plate containing an antibiotic, as described above. Absolutely no colony emerged, and it was confirmed that any *Agrobacteria* used for transformation were totally absent in the T1 plants.

Example 2

Confirmation of Phenotype of Progeny (T1) of Transformed *Fagopyrum esculentum* var. *Shinano* No. 1.

The flower of *Fagopyrum esculentum* var. *Shinano* No. 1 exerts the heterostylism, so pollination only occurs between different types of the flowers. Therefore, the flower of the transformed *Fagopyrum esculentum* var. *Shinano* No. 1 (TO) and the flower of the wild-type *Fagopyrum esculentum* var. *Shinano* No. 1 were pollinated. The seed consequently recovered was planted and grown to examine the phenotype of the T1 plants (FIG. 6). In both the *Fagopyrum esculentum* var. *Shinano* No. 1 introduced with the inventive gene toward the sense direction and *Fagopyrum esculentum* var. *Shinano* No. 1 introduced with the inventive gene toward the antisense direction, about halves of the progeny individuals (10 individuals) had individually inherited phenotypes of the T0 plants. In other words, branching was promoted in the progenies of *Fagopyrum esculentum* var. *Shinano* No. 1 introduced with the inventive gene toward the sense direction (2 in FIG. 6(A)). In contrast, branching and growth were suppressed in the progenies of *Fagopyrum esculentum* var. *Shinano* No. 1 with the inventive gene introduced toward the antisense direction (2 in FIG. 6(B)). As described above, the phenotypes of *Fagopyrum esculentum* var. *Shinano* No. 1 transformed with the inventive gene introduced toward the opposite directions to each other had also an opposite relation to each other from the respect of the progenies thereof.

Example 3

Confirmation of Integration of the Inventive Gene in Genome (1) Isolation and Purification of Genomic DNA from Progeny (T1) of Transformed *Fagopyrum esculentum* Var. *Shinano* No. 1.

Using Nuclear Phytopure DNA extraction kit (Amersham Pharmacia Biotec), genomic DNA was extracted from the seedlings or mature plants recovered in Example 2, according to the instruction. The extracted DNA was purified further by the following method. Specifically, DNA was dissolved in 10 mM Tris-HCl buffer (pH 8.0) containing 500 $\mu$l of 1 mM EDTA, which was then incubated with 2 $\mu$l of RNase (Nippon Gene; 10 mg/ml) at 37° C. for 45 minutes. Continuously, a solution of 100 $\mu$l containing 60 mM Tris-HCl buffer (pH 7.8), 60 mM EDTA, 30% SDS and 5 $\mu$l of Protease K (10 mg/ml) was added, for incubation at 50° C. for 3 hours. The solution was extracted sequentially in phenol, a phenol/chloroform mixture solution (1:1, v/v) and phenol. DNA was precipitated in ethanol from the resulting DNA solution, and was rinsed in 70% ethanol, to recover purified genomic DNA.

(2) Genomic Southern Hybridization

15 $\mu$g of the genomic DNA recovered above in (1) was digested with restriction endonucleases (utilizing EcoRI, SacI, XhoI and SalI, having no restriction sites in the cDNA of the MADS gene), followed by agarose (1%) electrophoresis and subsequent blotting on Hybond N+ nylon membrane (Amersham Pharmacia Biotec). A probe labeled with $^{32}$P was prepared by using the cDNA (1.3 kb) of the rice MADS box gene and a random primer labeling kit (manufactured by Takara), which was purified on a Sephadex G-50 column. The nylon membrane on which the DNA was blotted was first subjected to prehybridization in 5×SSPE solution (solution at pH 7.7, containing 0.18 M NaCl, 10 mM sodium phosphate, 1 mM EDTA), containing 5× Denhardt's solution, 0.5% SDS and 20 $\mu$g/ml salmon sperm DNA at 65° C. for one hour.

Subsequently, the probe labeled with $^{32}$P was added to the prehybridization solution, for hybridization at 65° C. for 18 hours. The membrane was rinsed twice in 2×SSPE solution containing 0.1% SDS at 20° C. for 10 minutes. Continuously, the membrane was rinsed once in 1×SSPE solution containing 0.1% SDS at 65° C. for 15 minutes. Finally, the membrane was rinsed twice in 0.1×SSPE solution containing 0.1% SDS at 65° C. for 10 minutes. The DNA band hybridizing with the probe was imaged by an image analyzer (Molecular Dynamics). The results are shown in FIGS. 7 and 8.

Figure 7:
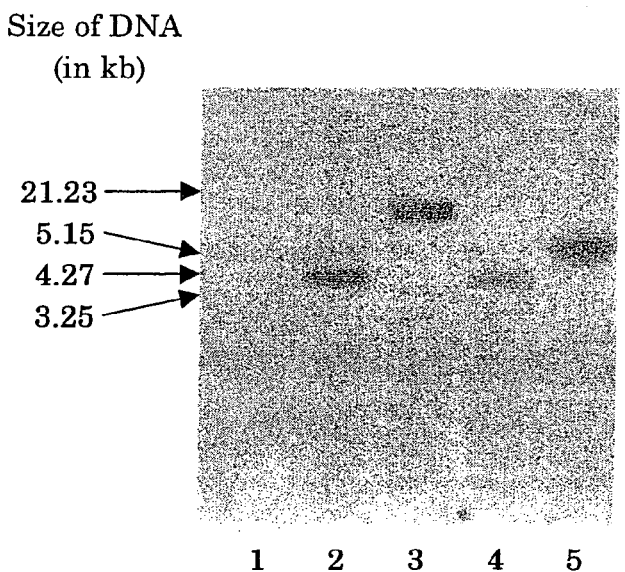
FIG. 7 is an image depicting the results of the genomic Southern hybridization of *Fagopyrum esculentum* var. *Shinano* No. 1 (T1) where the inventive gene is introduced toward the sense direction.

FIG. 7 depicts the progeny of *Fagopyrum esculentum* var. *Shinano* No. 1 with the inventive gene introduced toward the sense direction therein; and FIG. 8 depicts the progeny of *Fagopyrum esculentum* var. *Shinano* No. 1 with the inventive gene introduced toward the antisense direction therein. In both the figures, the lane 1 depicts the outcome of *Fagopyrum esculentum* var. *Shinano* No. 1 with no treatment, after digestion with EcoRI; the lane 2 depicts the outcome of the transformants, after digestion with EcoRI; the lane 3 depicts the outcome of the transformants, after digestion with SacI; the lane 4 depicts the outcome of the transformants, after digestion with XhoI; and the lane 5 depicts the outcome of the transformants, after digestion with SalI.

As apparently shown in FIGS. 7 and 8, no band was observed for *Fagopyrum esculentum* var. *Shinano* No. 1 with no treatment. However, only one hybridizing band was detected in all the lanes for each of both the genomic DNAs of the progeny of *Fagopyrum esculentum* var. *Shinano* No. 1 with the inventive gene inserted toward the sense direction (FIG. 7) and the progeny of *Fagopyrum esculentum* var. *Shinano* No. 1 with the inventive gene inserted toward the antisense direction (FIG. 8). Thus, it is indicated that one copy of the cDNA was introduced into the genomes of the T1 plants analyzed.

Example 4

Confirmation of Integration of the Inventive Gene into the Genome

For the amplification of the cDNA integrated into the genome, two types of PCR primers, namely P1 (SEQ ID NO: 3) and P2 (SEQ ID NO: 4), were designed.

```
P1:5'-ACAATCCCACTATCCTTCGC-3'

P2:5'-GTCACGACGTTGTAAAACGA-3'
```

Particularly, P1 corresponds to the 3' terminal sequence of the CaMV35S promoter positioned upstream the GUS gene in the original pBI121 binary vector; and P2 corresponds to a sequence in the proximity of the right border of T-DNA positioned downstream the GUS gene in the original pBI121 binary vector.

The genomic DNA (1–2 $\mu$l, 500 ng) prepared in Example 3(1) was added to a final 50-$\mu$l volume of a reaction solution (50 mM KCl, 10 mM Tris-HCl (pH 8.3), 1.5 mM MgCl$_2$, 200 $\mu$M each deoxynucleotide, 0.2 $\mu$M of the primers, and 1.25 units of Taq DNA polymerase (manufactured by Takara)). PCR reaction was conducted at 30 cycles of 94° C. for 30 seconds, 58° C. for 45 seconds and 72° C. for 90 seconds and was subsequently progressed at 72° C. for 10 minutes. The PCR products were subjected to agarose (1%) gel electrophoresis. After amplification, the reaction solution was directly applied to the electrophoresis and subsequently stained with ethidium bromide after electrophoresis.

Figure 9:
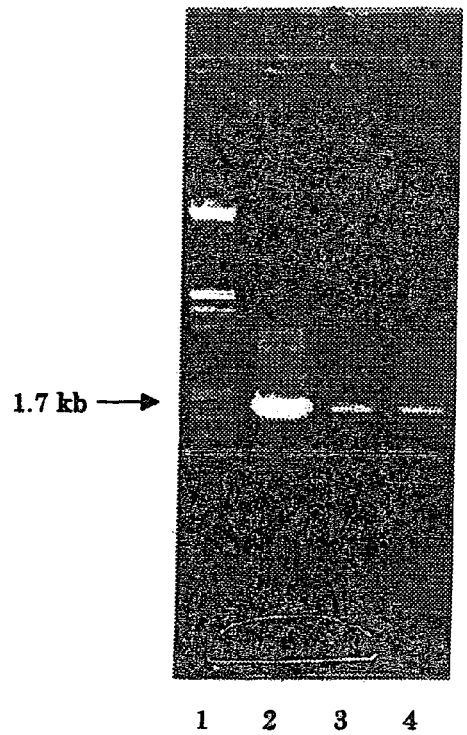
FIG. 9 is an image depicting the results of the electrophoresis, by which the integration of the inventive gene in the genome can be confirmed.

The results are shown in FIG. 9. In the figure, the lane 1 depicts the DNA size marker; the lane 2 depicts the PCR product of the vector with the inventive gene inserted toward the sense direction therein; the lane 3 depicts the PCR product of the genomic DNA derived from a plant transformed with the sense-directed inventive gene; and lane 4 depicts the PCR product of the genomic DNA derived from a plant transformed with the antisense-directed inventive gene.

FIG. 9 apparently shows that the DNA fragment of the predicted size (1.7 kb) in both the genomic DNAs was amplified and that the complete sequence of the cDNA was integrated in both the T1 plants.

Example 5

Confirmation of the Direction of cDNA Integrated in the Genome

Figure 10:
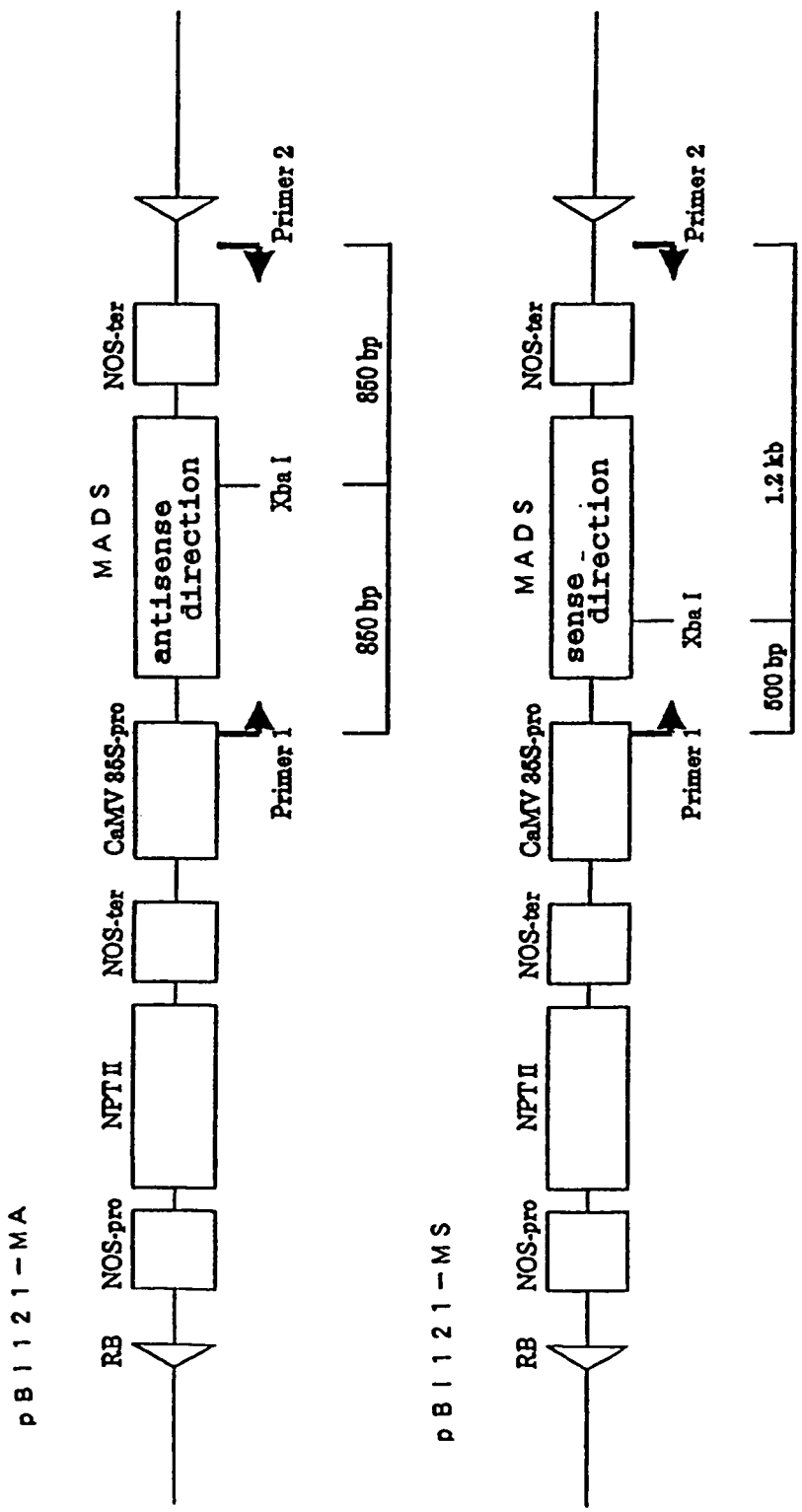
FIG. 10 shows diagrams schematically showing the MADS gene integrated toward the sense and antisense directions.

One restriction XbaI site is present at a position 472 bp from the 5' terminus of the inventive gene (1.3 kb). Taking account of the XbaI site of cDNA and the site where the PCR primers anneal, it is predicted that XbaI digestion of the PCR product will generate DNA fragments of 1.2 kb and 0.5 kb when the insertion is in the sense direction and will generate two fragments of 850 bp when the insertion is in the antisense direction (FIG. 10). The PCR products with the genomic DNAs from both the T1 plants and the PCR products with the two binary vectors carrying the cDNA used for the transformation were digested with XbaI and continuously subjected to Southern hybridization analysis using the $^{32}$P-labeled cDNA probe (FIG. 11).

Figure 11:
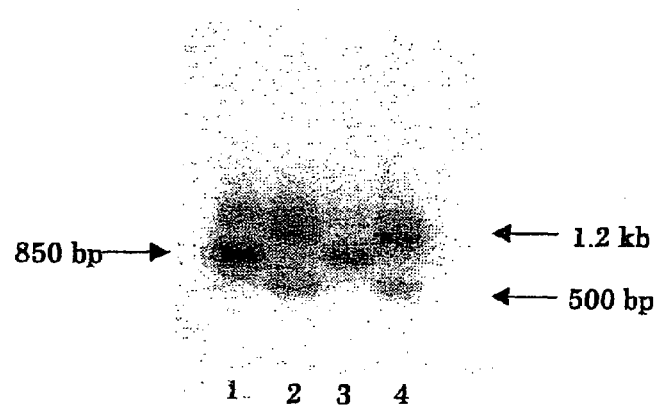
FIG. 11 is an image depicting the results of Southern hybridization analysis for the confirmation of the direction of the cDNA integrated in the genome.

In FIG. 11, "1" depicts the PCR product with the vector with the inventive gene inserted toward the antisense direction; "2" depicts the PCR product with the vector with the inventive gene inserted toward the sense direction; "3" depicts the PCR product of the genomic DNA derived from the plant transformed with the anti-sense-directed inventive gene; and "4" depicts the PCR product of the genome DNA derived from the plant transformed with the sense-directed inventive gene.

In FIG. 11, hybridizing bands of the predicted sizes were detected in the individual samples. The results show that cDNA was integrated toward the predicted directions in the genomes of the plants (T1) transformed toward the sense and antisense directions.

Example 6

Introduction of the Inventive Gene into *Kalanchoe daigremontiana*

A *Kalanchoe daigremontiana* mature leaf of a length of 10 to 13 cm was cut off from the stem. Using a stereomicroscope, several holes were punctured into the epidermal cells and mesophyll cells around the division cells in the utmost depth of an emarginate on the periphery of the leaf and the epidermal cells just above the division cells.

Each one drop of the aqueous suspension (1.0×10$^8$ cells/ml) of *A. tumefaciens* with the MADS gene introduced toward the sense direction therein, obtained in Example 1 (3) was inoculated into each emarginate part, by using a Pasteur pipette. Then, the leaf was left to stand for drying at ambient temperature for about 30 minutes. The leaf was placed on wet vermiculite placed in a plastic case, and then, the lid was closed for incubation at 25° C. (a cycle of 8-hour brightness and 16-hour darkness).

A fresh bud and root emerged from the treated part of the *Kalanchoe daigremontiana* leaf. After growing, these were cut off from the original leaf 4 weeks later and were photographed. As a control, a leaf treated with non-transformant *A. tumefaciens* and a leaf treated with *A. tumefaciens* with the GUS gene (beta-glucuronidase gene) introduced therein instead of the MADS gene were used. The results are shown in FIG. 12.

It was observed that leaves developed around the root of the stock transformed with the MADS box gene. However, no such phenomenon was observed in the control non-transformant and the stock with the GUS gene introduced therein instead of the MADS gene. The results show that the MADS box gene is a gene regulating branching, as in the test results using *Fagopyrum esculentum* var. *Shinano* No. 1. Because the MADS box gene regulates branching in not only *Fagopyrum esculentum* var. *Shinano* No. 1 but also *Kalanchoe daigremontiana* of a different species, the gene is suggested to be a gene capable of regulating branching in general plants.

What is claimed is:

1. A method for increasing plant branching comprising transforming a plant with an isolated rice MADS box gene, wherein said rice MADS box gene comprises SEQ ID NO:1 or comprises a rice MADS box gene encoding the polypeptide of SEQ ID NO:2.

2. The method of claim 1, wherein said rice MADS box gene comprises SEQ ID NO: 1.

3. The method of claim 1, wherein said rice MADS box gene is in a vector.

4. The method of claim 1, wherein said rice MADS box gene is in an expression vector and is operably linked to a promoter and a terminator.

5. The method of claim 1, wherein said rice MADS box gene is oriented in the sense direction.

6. A plant transformed with an isolated rice MADS box gene, wherein said rice MADS box gene comprises SEQ ID NO. 1 or comprises a rice MADS box gene encoding the polypeptide of SEQ ID NO: 2.

7. The plant of claim 6 wherein said rice MADS box gene comprises SEQ ID NO:1.

8. The plant of claim 6, wherein said rice MADS box gene is in a vector.

9. The plant of claim 6, wherein said rice MADS box gene is in an expression vector and is operably linked to a promoter and a terminator.

10. The plant of claim 6, wherein said rice MADS box gene is oriented in the sense direction.

11. The plant of claim 6, which is an ornamental plant.

12. The plant of claim 6, which is selected from the group consisting of chrysanthemum, lily, carnation, tulip, rose and orchidales.

13. The plant of claim 6, which is an agricultural plant.

14. The plant of claim 6 which is soybean.

15. The plant of claim 6 which is cotton.

16. The plant of claim 6 which is rice.

17. The plant of claim 6 which is maize.

18. The plant of claim 6 which is wheat or barley.

* * * * *